United States Patent [19]

Farrell

[11] Plant 4,565

[45] Jul. 8, 1980

[54] VARIETY OF TROPICAL APRICOT SHRUB

[76] Inventor: William R. Farrell, 2406 SW. 42 Ave., Ft. Lauderdale, Fla. 33317

[21] Appl. No.: 935,556

[22] Filed: Aug. 21, 1978

[51] Int. Cl.[2] ..... A01H 5/00

[52] U.S. Cl. ..... Plt./33

[58] Field of Search ..... Plt./33

*Primary Examiner*—Robert E. Bagwill
*Assistant Examiner*—James R. Feyrer
*Attorney, Agent, or Firm*—Malin & Haley

[57] ABSTRACT

A new variety of a tropical apricot shrub, originating as a sport bud variation from *Dovyalis abyssinica X hebecarpa,* or *D. hybrida* is known under the common name of tropical apricot. This new variety is characterized by variegated, color leaves having three distinct colorations of dark green, pale green disposed substantially centrally, and yellow disposed marginally about the leaves in a random variegated pattern.

3 Drawing Figures

BRIEF SUMMARY OF THE INVENTION

A new variety of tropical apricot shrub which is botanically a bud variation resulting as a sport, derived from *Dovyalis abyssinica X hebecarpa,* and belonging to the Flacourtiaceae family characterized by having a variegated (in color) leaf including the colors of dark green and pale green, randomly disposed in the central portion of the leaf with a yellow-greenish variegated border around the perimeter of the leaf. The sport plant was removed from the parent plant and said sport was asexually reproduced in Fort Lauderdale, Fla. by cuttings under mist producing identical plants.

DETAILED DESCRIPTION OF MY NEW PLANT VARIETY

Figure 1:
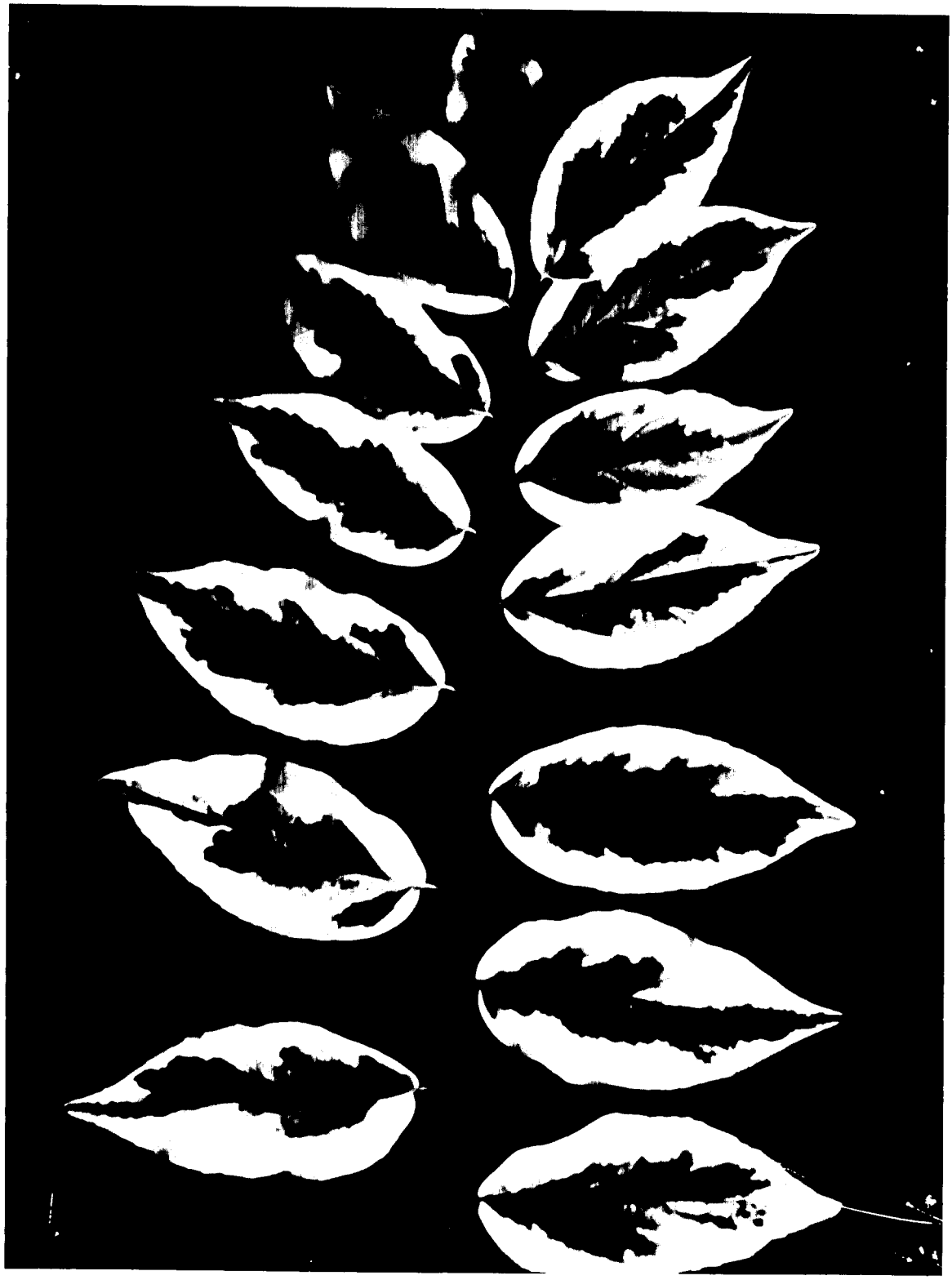
FIG. 1 is a photograph of a branch showing my new plant variety.

The new sport shown herein has a simple 3 inch to 4 inch long ovate leaf with approximately a quarter inch exstipulated petiole. The venation of the leaf blade is pinnate. The leaf margin is serrate to serrulate, tip weakly acuminate, to acute, obtuse base slightly oblique on some leaves. Leaf arrangement (phyllotaxis) on a simple stem is alternate with one leaf at a node. The stem has pronounced lenticels. The leaf surface is glabrous, with underside pubescent on veins.

The new sport plant has good strong, vigorous growth, with no known disease or insect problems. Large plants have been observed to withstand some freezing down to 26 degrees Faharenheit for a short time (4 to 6 hours without much damage).

With respect to the new sport growth habits, a large, spreading evergreen shrub 15 feet by 15 feet, will become wider than the height, with long drooping branches if left unattended. The sport shrub has softly weeping stems that lay like feathers (FIG. 3) with its leaves lying flat across in its alternate position on the stem.

Asexual propagation has been accomplished by cutting and air layering. The applicant has been very successful with these methods with the new sport striking roots readily. Propagation from seed germination is unknown, due to lack of fruit set, up to this date on the new sport plant.

Flower inflorescences appear visually identical to the parent plant. The parent plant, having a perfect flower, sets fruit, while the new sport plant, although having flowered while planted in containers, has not set fruit up to this time. Flowers are produced in the new sport plant on the axils of leaves. A cluster of flowers of one to five or more will appear.

With respect to morphological characteristics, the new sport plant appears identical to its parent, with the exceptions of the noted leaf variegation and the softly weeping stems and leaves. The parent plant has dark green leaves and the stems are more rigid, with a leaf blade that is strongly undulated. This leaf, being strongly undulated, causes the leaf to "cup " or to have the leaf turn upward from the midrib.

The coloration on the leaf in accordance with the ISCC-NBS color designation system, would include in the central portion of the leaf, a dark green number 146 mixed randomly in the center portion with a light green 144 with the dark green and light green being surrounded by a light greenish-yellow 119 extending out to the perimeter of the leaf.

Figure 2:
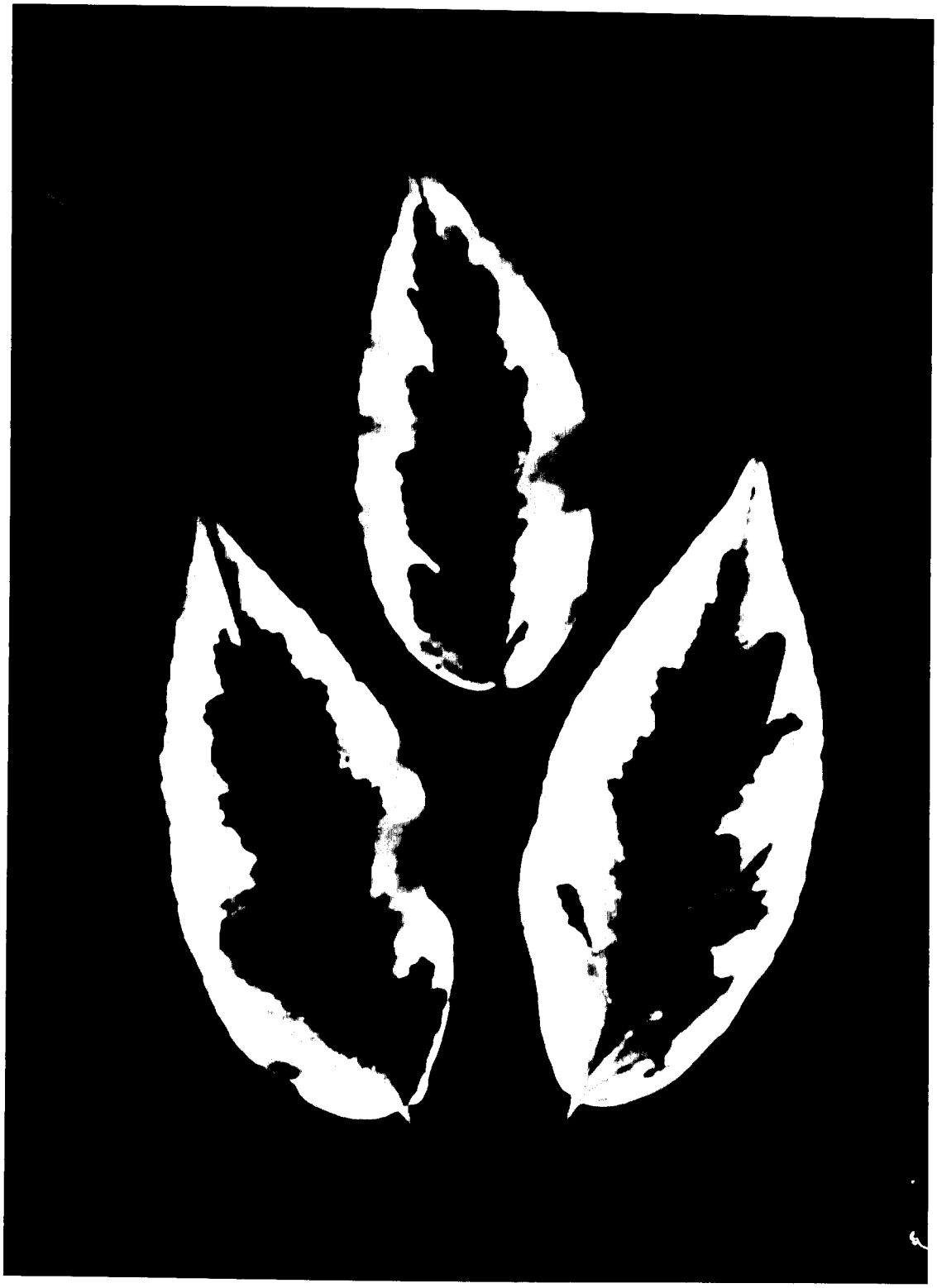
FIG. 2 shows three separate leaves showing my new variety of plant.
Figure 3:
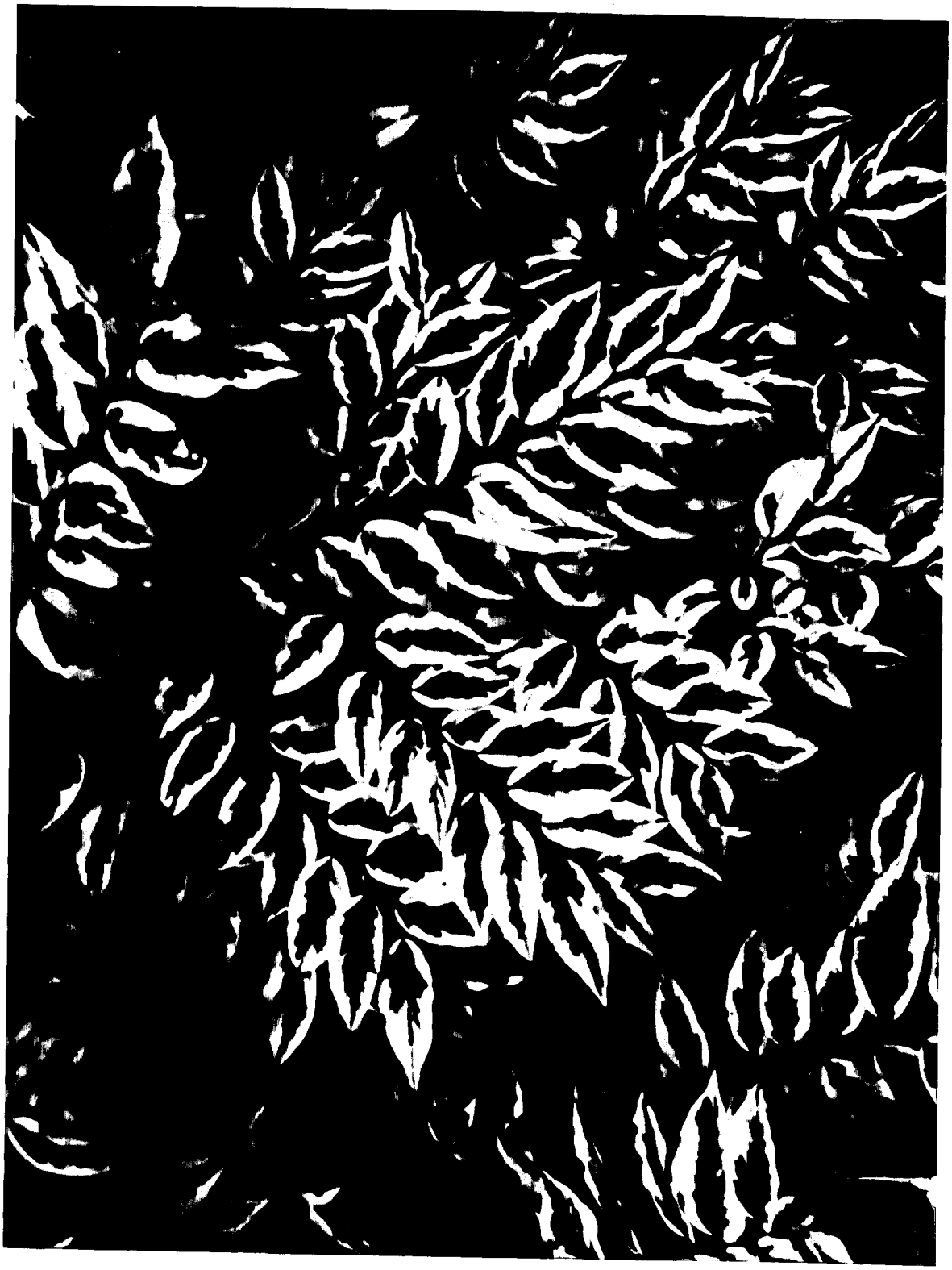
FIG. 3 shows a photograph of a plurality of branches showing my new plant variety.

Referring now to the FIGS. 1, 2, and 3, my new variety of plant is shown as being characterized by having a very distinctive and unique coloration on each leaf. Looking at FIGS. 1 and 2, for example, each leaf has a pale yellow boarder and randomly disposed dark and light green areas in the central area along the main leaf stem. The light green coloring includes various degrees of greenish-yellow interdisposed among distinctive dark green patterns of which are somewhat randomly disposed.

FIG. 3 shows the effect of the entire bush with the distinctive coloration shown on the leaves. The size of each dark and light green area on the central portion of the leaf varies from leaf to leaf.

What I claim is:

1. A new and distinct variety of tropical apricot shrub substantially as described and illustrated having a leaf that is characterized by a central portion of dark and light green areas and a yellow perimeter surrounding the central portion.

* * * * *